United States Patent [19]

Brown

[11] Patent Number: 5,504,240

[45] Date of Patent: Apr. 2, 1996

[54] BORANE-HYDROXYDIALKYLSULFIDE BORATES

[75] Inventor: Herbert C. Brown, West Lafayette, Ind.

[73] Assignee: Aldrich Chemical Company, Inc., Milwaukee, Wis.

[21] Appl. No.: 437,583

[22] Filed: May 9, 1995

[51] Int. Cl.$^6$ ........................................... C07F 5/04
[52] U.S. Cl. ........................................... 558/295
[58] Field of Search ........................................... 558/295

[56] References Cited

FOREIGN PATENT DOCUMENTS 54-59232  5/1979  Japan.

Primary Examiner—Robert Gerstl
Attorney, Agent, or Firm—Niblack & Niblack

[57] ABSTRACT

Novel borane adducts of hydroxydialkylsulfide borate esters represented by formula $$[RS(CH_2CH_2O)_n]_3B$$
$$|$$
$$BH_3$$

wherein R is straight or branched chain alkyl or alkoxy having from 2 to 5 carbon atoms and n is 1 to 3 inclusive. The compound are new hydroboration agents.

10 Claims, No Drawings

BORANE-HYDROXYDIALKYLSULFIDE BORATES

BACKGROUND OF THE INVENTION

1. Field of Invention

The present invention provides a novel class of borane-sulfide hydroboration agents, their methods of production and their use in the hydroboration and reduction of organic compounds. More particularly, this invention provides novel borane adducts of hydroxydialkylsulfide borates which have a number of advantages over the presently available agents.

2. Prior Art

Borane carriers are of increasing importance with the growing applications of diborane in the synthesis of pharmaceuticals and other important compounds.

Borane-tetrahydrofuran is a valuable reagent for the hydroboration of olefins and for the reduction of organic compounds. It suffers from the disadvantage in that the solutions are unstable over a period of time. U.S. Pat. No. 3,882,037 discloses stabilized borane-tetrahydrofuran solutions which permit storage of such solutions for relatively longer periods of time. However, the inherent availability only as a relatively dilute solution in tetrahydrofuran poses a serious drawback to the commercial use of this reagent.

Borane-methyl sulfide (BMS) is much more stable than borane-tetrahydrofuran and is widely used for both hydroboration and reduction [See Burg et al., *J. Am. Chem. Soc.* 76, 3307 (1954) and Coyle et al., *J. Am. Chem. Soc.* 81, 2989 (1959)]. However, it suffers from the serious disadvantage in that it yields a product which contains free dimethyl sulfide. The free dimethyl sulfide is highly volatile, b.p. 38° C., flammable and has a very noxious odor. Moreover, it is not soluble in water, so it cannot be disposed of by washing it away with water.

Borane-1,4-thioxane (U.S. Pat. No. 4,298,750) is another valuable hydroboration agent. It has both lower volatility and milder odor than dimethyl sulfide. It has a limited solubility in water and can be easily oxidized to the corresponding sulfoxide, which is miscible in water. This agent is a liquid, 8M in $BH_3$, stable over prolonged periods. Unfortunately, this commercially available reagent is relatively costly compared to borane-tetrahydrofuran and borane-dimethyl sulfide. Thus, the search continues for effective, versatile borane-sulfide derivatives which are as effective as the commercially available reagents but which overcome the disadvantages of noxious odor, expense, volatility, and lack of water solubility. The present invention fulfills this long-standing need.

SUMMARY OF THE DISCLOSURE

The present invention provides novel borane adducts of hydroxydialkylsulfide borate esters represented by formula I

wherein R is straight or branched chain alkyl or alkoxy having from 2 to 5 carbon atoms and n is 1 to 3 inclusive.

The products are liquids and readily hydroborate representative olefins, such as 1-octene, β-pinene, 1-methylcyclohexene, 2,3-dimethylbutene, and the like. They are readily treated with water to hydrolyze the borate ester with removal of the hydroxydialkylsulfide intermediate. The compounds of this invention exhibit insignificant odor and are therefore useful for large-scale hydroboration applications.

In the practice of this invention, an efficient, one-pot procedure for the formation of both the borate ester, represented by formula II

and subsequent formation of the borane adducts (Formula I above is provided. Generally speaking, refluxing an appropriate hydroxysulfide and boric acid in molar ratio 3:1 in toluene and distilling off toluene and water gave borate esters (formula I) in more than 90% yields (6 h). Formation of borate esters ere confirmed by $^{11}$B NMR ($\delta$ 17–18) and downfield movements of the $CH_2$ attached to the O—B bond from $\delta$ 3.7 to $\delta$ 3.9 accompanying ester formation.

Alternatively, borate esters were prepared from the reaction of borane-tetrahydrofuran with hydroxysulfide in molar ratio 1:3. Quantitative borate ester formation was confirmed by measuring the hydrogen evolved. Warming of the reaction mixture (60°–65° C.) is necessary to drive the reaction to completion. Generally speaking, the novel compounds of this invention are conveniently prepared in a straight-forward procedure by passing diborane into a neat borate ester at 0° C. in a bubbler provided with a stirrer. Excess diborane not absorbed by the borate ester is absorbed in a downstream bubbler containing tetrahydrofuran over mercury and cooled in ice water. A mercury bubbler is connected to the exit. Diborane is passed into the ester until the concentration of excess borane in THF reaches approximately 1 M. The borane-borate adduct is stirred overnight at room temperature prior to disconnecting the bubblers and analyzed for active hydride following the procedure described by Brown, H. C., *Organic Syntheses via Boranes*, J. Wiley: New York, 1975, p. 191, using a 2M hydrochloric acid-glycerol-water (2:1:1) hydrolysis solution.

The complexing ability of the borane adducts toward borane was tested by the exchange of BMS (borane-methylsulfide) and $BH_3$.THF (borane- tetrahydrofuran) mixed in 1:1 molar ratio. The amount of borane taken by a borate in the equilibrium was determined by $^{11}$B NMR and is shown in the Table following the examples. Values for the exchange with borane-tetrahydrofuran, a 1M solution, should be considered less quantitative since THF is in large excess.

The borane adducts of this invention are highly reactive, hydroborating 1-octene is tetrahydrofuran at room temperature in less than 1 hour. A number of the adducts are liquids above 0° C. The adducts are soluble in diethyl ether, tetrahydrofuran and dichloromethane. Adducts kept at room temperature for one week did not show any observable change in molarity, indicating the stable nature of the products.

The hydroboration of 1-octene with all representative borane adducts under neat conditions was carried out at room temperature. The results are shown in Table 2. As revealed by $^{11}$B NMR, all adducts hydroborate 1-octene, showing a quantitative transformation to trioctyl borane in approximately 15 minutes.

The preparation of representative borane-amine adducts of this invention are illustrated in the following examples.

DETAILED DESCRIPTION OF PREFERRED EMBODIMENTS

All manipulations and reactions with air-sensitive compounds were carried out under a nitrogen atmosphere. All glassware was oven-dried for several hours, assembled while hot and cooled in a stream of dry nitrogen gas. Syringes were assembled and fitted with needles while hot. Techniques for handling air-sensitive compounds under nitrogen atmosphere are described in Brown, H. C., *Organic Syntheses Via Boranes*, J. Wiley; New York, 1975, p. 191. $^1$H, $^{13}$C and $^{11}$B NMR spectra were recorded on a Varian Gemini 300 multinuclear instrument. The $^{11}$B NMR chemical shifts are δ relative to $BF_3.OEt_2$. Mass spectra were taken on a 4000 Finnigan MAT spectrometer. Optical rotations were measured on a Rudolph automatic polarimeter Autopol III. GC analyses were carried out on a Varian 3300 chromatograph (catharometer) equipped with a 12 ft×0.125 in column packed with 10% SE-30 polyethylene glycol (Union Carbide) on Chromosorb W 100–120 mesh). Microanalysis were performed at the Microanalytical Laboratory, Purdue University, West Lafayette, Ind., USA.

Borane-methyl sulfide (BMS), 2-mercaptoethanol, alkyl mercaptan, chlorohydrin and boric acid were commercial products (Aldrich Chemical Company, Milwaukee, Wis., USA). 1-Octene and (−)-β-pinene were distilled prior to use from a small amount of lithium aluminum hydride under vacuum.

Example 1

General Procedure for Synthesis of Hydroxysulfides Intermediates

Sodium methoxide (10.80 g, 200 mmol) was dissolved in methanol (100 ml). Alkylmercaptan (200 mmol) was added and the mixture was left a room temperature for 1 h. Chlorohydrin (200 mmol) was added, the mixture was warmed to reflux and refluxed for 1 h. Precipitated sodium chloride was filtered off and washed with methanol. The methanol was removed from the filtrate under vacuum. Diethyl ether (50 ml) was added and a small amount of sodium chloride was filtered off. The product was isolated by distillation under vacuum. The following intermediates were prepared in this fashion: 2-(tert-butylthio)ethanol; 2-(isoamylthio)ethanol; 2-[2-(ethylthio)ethoxy]ethanol; 2-[2-(tert-butylthio)ethoxy]ethanol; 2-[2-(isoamylthio)ethoxy]ethanol; 2-[2-[2-(methoxyethylthio)ethoxy]ethoxy] ethanol; 2-[2-[2-(isoamylthio)ethoxy]ethoxy] ethanol; and 2-(2-(methoxyethylthio) ethanol. Literature preparations for these starting hydroxy sulfides include: Sherlin, S. M. et al., *J. Prakt. Chem.* [2] 1933, 138, 23; Strauss, C. R. et al., *J. Org. Chem.* 1964, 29, 1945; Shostakovskii, M. E. et al., *Izv. Akad. Nauk SSSR, Ser. Khim.* 1965, 11, 2049–2051; Atavin et al. *Zh. Organ. Khim.* 1966, 2, 14–17.

Example 2

Thiodiethanol Monomethyl Ether

Sodium methoxide (10.88 g, 0.22 mol) was dissolved in methanol (100 ml) and 2-mercaptoethanol (15.63 g, 0.2 mol) was added and the mixture was left for 1 h at room temperature. 2-Chloroethyl methyl ether (20.80 g, 0.22 mol) was added and the mixture was refluxed for 1 h. Sodium chloride was filtered off and the product was isolated by distillation: 25.06 g, (92%), bp 64°–65° C./0.1 mm Hg.

Example 4

Quantitative Generation of Diborane

A 50-ml one-neck, round-bottom flask provided with a septum inlet, magnetic stirring bar and an adapter with a stopcock was charged with boron trifluoride-diglyme or -triglyme adduct (75 mmol). A 2M solution of sodium borohydride in triglyme (28.5 ml, 57 mmol) was added dropwise by means of a hypodermic syringe. Generation of diborane is smooth and the reaction is not exothermic. After the addition was completed, the flask was heated to 100° C. and kept at this temperature for 15 min. Diborane was absorbed in tetrahydrofuran (30 ml) at 0° C. Analysis of the $BH_3$.THF solution obtained for active hydride according to a standard procedure described in Brown, H. C., *Organic Syntheses via Boranes*; J. Wiley: New York, 1975, p. 241, showed 2.37M concentration of borane (95% yield); $^{11}$B NMR, δ, +1.0 ppm.

Example 5

Tris[2-(tert-butylthio)ethyl]borate (8a)

Diborane (12 mmol) generated as described in Example 4 was passed through a bubbler containing sodium borohydride (0.1 g) in diglyme (5 ml) and a trap cooled to −78° C. was absorbed in neat 2-(tert-butylthio)ethanol (4.70 g, 35 mmol) at room temperature. The hydrogen evolved was exited through a vent. Generation of diborane is smooth and the reaction is not exothermic. After the addition was complete, the solution of borate was stirred at 50° for 30 min under a slow stream of nitrogen to obtain the borate ester. $^{11}$B NMR δ 17.67. $^1$H NMR ($CDCl_3$) δ 1.323 (s, 9H, $CH_3$), 2.69, t,J=6.9 Hz, 2H, $CH_2$), 3.89 (t, J=6.9 Hz, 2H, $CH_2$; $^{13}$C NMR ($CDCl_3$) δ 29.80 ($CH_3$), 31.12 ($CH_2$), 42.02 (C), 63.41 ($CH_2$), MS (70 eV EI CI)411 (M+1, 25), 277(58), 221(54), 135 (64).

Example 6

Tris[2-(Isoamylthio)ethyl]borate (8b)

Diborane (12 mmol) generated as described in Example 4 was passed through a bubbler containing sodium borohydride (0.1 g) in diglyme (5 ml) and a trap cooled to −78° C. was absorbed in neat 2-(isoamylthio)ethanol (35 mmol) at room temperature. The hydrogen evolved was exited through a vent. Generation of diborane is smooth and the reaction is not exothermic. After the addition was complete, the solution of borate was stirred at 50° for 30 min under a slow stream of nitrogen to obtain the borate ester. $^1$H NMR ($CDCl_3$) δ 0.90 (d,J=6.6 Hz, 6H, $CH_3$), 1.48 (q, J= 6.6 Hz, 2H, $CH_2$), 1.62 (nonet, J=6.6 Hz, 1H, CH), 2.55 (t, J= 6.8 Hz, 2H, $CH_2$), 2.70 (t,J=6.8 Hz, 2H, $CH_2$), 3.92 (t, J= 6.8 Hz, 2H, $CH_2$); $^{13}$C NMR ($CDCl_3$) δ 22.32 ($CH_3$), 27.41 (CH), 30.28 ($CH_2$), 33.19 ($CH_2$), 38.78 ($CH_2$), 62.84 ($CH_2$) MS (70 eV EI CI) 453 (M+1, 28), 305(100), 131(52).

Example 7

Tris[2-[2-(Ethylthio)ethoxy]ethyl]borate (8c)

The title compound was prepared by the method of Example 6, substituting 2-[2[(ethylthio)ethoxy]ethanol for 2-(isoamylthio)ethanol. $^1$H NMR ($CDCl_3$) δ 1.25 (t,J=7.1 Hz, 3H, $CH_3$), 2.59 (q, J=7.1 Hz, 2H, $CH_2$), 2.72 (t,J=6.8 Hz, 2H, $CH_2$), 3.57 (t,J=6.8 Hz, 2H, $CH_2$), 3.65 (t,J=6.8 Hz, 2H, $CH_2$), 3.94 (t,J=6.8 Hz, 2H, $CH_2$); $^{13}$C NMR ($CDCl_3$) δ 14.89 ($CH_3$), 26.35 ($CH_2$), 31.03 ($CH_2$), 62.71 ($CH_2$), 70.93 ($CH_2$), 71.27 ($CH_2$); MS (70 eV EI CI) 459 (M+1), 309(60), 89(100).

Example 8

Tris[2-[2-(tert-Butylthio)ethoxy]ethyl]borate (8d)

The title compound was prepared by the method of Example 6 from 2-[2-(tert-butylthio)ethoxy]ethanol. $^1$H NMR (CDCl$_3$) δ 1.32 (s, 9H), 2.62 (t,J=6.9 Hz, 2H, CH$_2$), 3.54 (t, J=6.9 Hz, 2H, CH$_2$), 3.62 (t,J=6.7 Hz, 2H, CH$_2$), 3.92 (t,J=6.7 Hz, 2H, CH$_2$); $^{13}$C NMR (CDCl$_3$) δ 28.04 (CH$_3$), 41.03 (CH$_2$), 32.01 (C), 62.75 (CH$_2$), 71.01 (CH$_2$), 71.33 (CH$_2$); MS (70 eV EI CI) 543 (M+ 1), 365(24), 117(100).

Example 9

Tris[2-[2-(Isoamylthio)ethoxy]ethyl]borate (8e)

The title compound was prepared by the method of Example 6 from 2-[2-(isoamylthio)ethoxy]ethanol. $^1$H NMR (CDCl$_3$) δ 0.90 (d,J= 6.8 Hz, 6H, CH$_3$), 1.49 (q,J=6.7 Hz, 2H, CH$_2$), 1.64 (nonet, J= 6.7 Hz, 1H, CH), 2.54 (t,J=6.7 Hz, 2H, CH$_2$), 2.70 (t,J=6.7 Hz, 2H, CH$_2$); 3.54 (t,J=6.5 Hz, 2H, CH$_2$), 3.64 ((t,J=6.5 Hz, 2H, CH$_2$), 3.91 (t,J=6.5 Hz, 2H, CH$_2$); $^{13}$C NMR (CDCl$_3$) δ 22.30 (CH$_3$), 27.36 (CH), 30.53 (CH$_2$), 31.44 (CH$_2$), 38.75 (CH$_2$); 62.73 (CH$_2$), 70.91 (CH$_2$), 71.29 (CH$_2$); MS (70 eV EI CI) 585 (M+1, 14), 393(97), 131(100).

Example 10

Tris[2-[2-[2-(Ethylthio)ethoxy]ethoxy]ethyl borate (8f)

The title compound was prepared by the method of Example 6 from 2-[2-[2-(ethylthio)ethoxy]ethoxy]ethanol. $^1$H NMR (CDCl$_3$) δ 1.25 (t,J=6.9 Hz, 3H, CH$_3$), 2.56 (q, J=6.9 Hz, 2H, CH$_2$), 2.70 (t,J=6.3 Hz, 2H, CH$_2$), 3.65 (m,J=5.7 Hz, 8H, CH$_2$); 3.93 (t, J=6.7 Hz, 2H, CH$_2$); $^{13}$C NMR (CDCl$_3$) δ 14.90 (CH$_3$), 26.30 (CH$_2$), 30.90 (CH$_2$), 62.68 (CH$_2$), 70.34 (CH$_2$); 70.47 (CH$_2$); 71.02 (CH$_2$), 71.64 (CH$_2$); MS (70 eV EI CI) 591 (M+1, 2), 397(100), 89(25).

Example 11

Tris[2-[2-[2-(tert-Butylthio)ethoxy]ethoxy]ethyl]borate (8g)

The title compound was prepared from 2-[2-[2-(tert-butylthio)ethoxy]ethoxy]ethanol by the method of Example 6. $^1$H NMR (CDCl$_3$) δ 1.32 (s, 9H, CH$_3$), 2.74 (t,J=6.3 Hz, 2H, CH$_2$), 3.64 (m, J=6.3 Hz, 8H, CH$_2$), 3.91 (t,J=6.3 Hz, 2H, CH$_2$); $^{13}$C NMR (CDCl$_3$) δ 27.89 (CH$_3$), 31.01 (CH$_2$), 42.02 (C), 62.67 (CH$_2$), 70.33 (CH$_2$); 70.44 (CH$_2$); 71.17 (CH$_2$), 71.64 (CH$_2$); MS (70 eV EI CI) 675 (M+1), 453(19), 117(100).

Example 12

Tris[2-[2-[2-(Isoamylthio)ethoxy]ethoxy]ethyl]borate (8h)

The title compound was prepared from 2-[2-[2-(isoamylthio)ethoxy]ethoxy]ethanol by the method of Example 6. $^1$H NMR (CDCl$_3$) δ 0.90 (d, J=6.3 Hz, 6H, CH$_3$), 1.46 (q,J=6.3 Hz, 2H, CH$_2$), 1.64 (nonet, J=6.3 Hz, 1H, CH), 2.52 (t,J=6.6 Hz, 2H, CH$_2$), 2.71 (t,J=6.6 Hz, 2H, CH$_2$), 3.64 (m, J=6.6 Hz, 8H, CH$_2$), 3.91 (t,J=6.6 Hz, 2H, CH$_2$); $^{13}$C NMR (CDCl$_3$) δ 22.29 (CH$_3$), 27.38 (CH), 30.52 (CH$_2$), 31.31 (CH$_2$), 38.76 (CH$_2$); 62.68 (CH$_2$), 70.35 (CH$_2$); 70.47 (CH$_2$), 71.06 (CH$_2$), 71.65 (CH$_2$); MS (70 eV EI CI) 717 (M+1), 482(22), 481(100), 131(85).

Example 13

Tris[2-(2-Methoxyethylthio)ethyl]borate (8i)

The title compound was prepared from 2-(2-methoxyethylthio)ethanol by the method of Example 6. $^1$H NMR (CDCl$_3$) δ 2.71 (m, J=6.2 Hz, 4H, CH$_2$), 3.38 (s, 3H), 3.56 (t, J= 6.2 Hz, 2H, CH$_2$), 3.92 (t,J=6.2 Hz, 2H, CH$_2$); $^{13}$C NMR (CDCl$_3$) δ 31.58 (CH$_2$), 33.55 (CH$_2$), 58.68 (CH$_2$), 62.83 (CH$_2$), 62.83 (CH$_2$); 72.19 (CH$_3$); MS (70 eV EI CI) 417 (M+1, 14), 385(15), 281(33), 137(24), 119(20).

Example 14

Tris[2-(tert-Butylthio)ethyl]borate borane adduct (1:3) (9a)

A 100 ml one-neck, round-bottom flask equipped with a septum inlet, magnetic stirring bar and an adapter with a stopcock was charged with boron trifluoride diglyme (20 mmol). A 2M solution of sodium borohydride in triglyme (7.5 ml, 15 mmol) was added dropwise by means of a hypodermic syringe. Generation of diborane is smooth and the reaction is not exothermic. Generated diborane was passed through a bubbler containing sodium borohydride (0.1 g) in diglyme (5 ml) and a trap cooled to −78° C. was absorbed in neat 2-(tert-butylthio)ethanol (7.94 g, 60 mmol) at room temperature. After the addition was completed, the solution of borate was stirred at 50° C. for 15 min under a slow stream of nitrogen to produce the borate ester tris[2-(tert-butylthio)ethyl borate at room temperature. Escaped diborane was absorbed in the following bubbler containing tetrahydrofuran (10 ml) over mercury and cooled in ice water. A mercury bubbler was connected to the exit. Diborane was passed into the solution until the concentration of borane in the THF reached approximately 1M. The borane adduct, a colorless liquid, was analyzed for active hydride by a standard procedure using a water:glycerol:THF 1:1:1 hydrolyzing mixture. Concentration 6.4 M, $^{11}$B NMR δ −26.03.

Examples 15–22

Following the process of Example 14, the following borane adducts were produced:

tris[2-Isoamylthio)ethyl]borate borane adduct (1:3) (9b) from tris-(2-isoamylthio)ethyl]borate (8b);

tris[2-[2-(Ethylthio)ethoxy]ethyl]borate borane adduct (1:3) (9c) from tris[2-[2-(ethylthio)ethoxy]ethyl]borate (8c);

tris[2-[2-(tert-Butylthio)ethoxy]ethyl]borate borane adduct (1:3) (9d) from tris[2-[2-(tert-butylthio)ethoxy]ethyl]borate (8d);

tris[2-[2-(Isoamylthio)ethoxy]ethyl borate borane adduct (1:3) (9e) from tris[2-[2-(isoamylthio)ethoxy]ethy]borate (8e);

tris[2-[2-[2-(Ethylthio)ethoxy]ethoxy]ethyl]borate borane adduct (1:3) (9f) from tris[2-[2-[2-(ethylthio)ethoxy] ethoxy]ethyl]borate (8f);

tris[2-[2-[2-(tert-Butylthio)ethoxy]ethoxy]ethyl]borate borane adduct (1:3) (9g) from tris[2-[2-[2(tert-butylthio)ethoxy] ethoxy]ethyl]borate (8g);

tris[2-[2-[2-(Isoamylthio)ethoxy]ethoxy]ethyl]borate borane adduct (1:3) (9h) from tris[2-[2-[2(isoamylthio)ethoxy] ethoxy]ethyl]borate (8h);

tris[2-(2-Methoxyethylthio)ethyl]borate borane adduct (1:3) (9i) from tris[2-(2-methoxyethylthio)ethyl]borate (8i).

Example 23

Representative General Procedure for Hydroboration of 1-Octene With Borane-Borate Adducts A 6.9M borane adduct (9i) (3 ml, 18 mmol) was dissolved in dichloromethane (18 ml) and 1-octene (3.36 g, 30 mmol) was added dropwise with stirring at 25°–28° C. The progress of the reaction was monitored by $^{11}$B NMR. The reaction was completed when the borane-amine signal (quartet) disappears and the trioctylborane signal (singlet, δ 86 ppm) was the only one in the spectrum. The solvent was separated, dried over anhydrous magnesium sulfate and octanol was isolated by distillation to yield 6.24 g, bp 99°– 100° C./20 mm Hg. GC analysis (Carbowax 20) showed 1-octanol (94%) and 2-octanol (6%).

Example 24

(−)-cis-Myrtanol

A 6.0M borane adduct (9i) was dissolved in dichloromethane (12 ml) and (−)-β-pinene (5.0 g, 26 mmol), 91% ee was added at 0° C. The reaction was completed in 0.5 h, as indicated in $^{11}$B NMR. The mixture was maintained at room temperature for 1 h and oxidized by the addition of 3M sodium hydroxide (5.6 ml, 17 mmol) and 30% hydrogen peroxide (4.0 ml, 40 mmol), keeping the temperature during the addition below 30° C. and then stirring at room temperature overnight. The dichloromethane layer was separated and stirred with water (20 ml) for 0.5 h. The organic layer was separated, dried over anhydrous magnesium sulfate and distilled to give 5.05 g (91%) of pure product, bp 116°–118° C./15 mm Hg. $[\alpha]^{20}D=-19.4°$.

Example 25

Hydroboration of 1-Methylcyclohexene

Following the procedure of Example 24, 1-methylcyclohexene (1.15 g, 12 mmol) was added dropwise with stirring to a 6.0M solution of 8i (1 ml, 6 mmol). The reaction mixture was maintained at room temperature for 0.5 h with stirring. Ethanol (1 ml) was added slowly with stirring at 0° C. $^{11}$B NMR δ 53 was noted.

Example 26

Hydroboration of Thexylene

Following the procedure of Example 24, thexylene (0.504 g, 6 mmol) was added dropwise to a 6.0M solution of borane adduct 8i with cooling to maintain the temperature at 20°–25° C. The reaction mixture was allowed to stir at room temperature for 0.5 h. $^{11}$B NMR δ 24.33 for thexylborane was noted.

As can be seen by the examples, the compounds of this invention hydroborate a wide spectrum of olefins including terminal di-, tri- and tetrasubstituted olefins.

The hydroboration of 1-octene with representative borane adducts under neat conditions was carried out at room temperature. The results are shown in the following Table. As revealed by $^{11}$B NMR, all adducts hydroborate 1-octene, showing a quantitative transformation to trioctylborane in approximately 15 minutes. As can also be seen by the Table, the complexing ability of the borate esters, compared to the standard, well-known reagent, BMS, exchange between BMS and borate ester was carried out and followed by $^{11}$B NMR. The amount of borane taken by the borate esters from BMS at equilibrium for 1:3 mixtures is presented in the following table.

As can be seen by the data, the borane adducts of this invention are liquids and all hydroborate 1-octene in 15 minutes. Thus, they are desirable hydroboration agents.

TABLE 1

| Hydroxysulfides | | |
|---|---|---|
| hydroxysulfides | odor | solubility in water 1 g per . . . mL $H_2O$ |
| t-BuSCH$_2$CH$_2$OH | mild | 50 |
| i-AmSCH$_2$CH$_2$OH | agreeable; strong | <100 |
| EtSCH$_2$CH$_2$OCH$_2$CH$_2$OH | very mild | miscible |
| t-BuSCH$_2$CH$_2$OCH$_2$CH$_2$OH | mild | 15 |
| i-AmSCH$_2$CH$_2$OCH$_2$CH$_2$OH | agreeable; weak | <100 |
| Et—SCH$_2$CH$_2$OCH$_2$CH$_2$OCH$_2$CH$_2$OH | very mild | miscible |
| t-BuSCH$_2$CH$_2$OCH$_2$CH$_2$OCH$_2$CH$_2$OH | mild | miscible |
| i-AmSCH$_2$CH$_2$OCH$_2$CH$_2$OCH$_2$CH$_2$OH | agreeable; weak | ~100 |
| H$_3$COCH$_2$CH$_2$SCH$_2$CH$_2$OH | mild | miscible |

TABLE 3

Borane Adducts of Borate Esters of Hydroxydialkylsulfides

| | exchange,[a] % | | borane addition compounds of borate esters | | | | |
|---|---|---|---|---|---|---|---|
| sulfur substituted borate ester | BMS | BH$_3$.THF | state | [BH$_3$][b] M | $^{11}$B NMR,[c] δ borate | adduct | HB of 1-octene[d] |
| i-BuSCH$_2$CH$_2$OH (8a) | 8 | 68 | (9a) liquid | 6.4 | 17.67 | −26.03 | 15 min |
| i-AmSCH$_2$CH$_2$OH (8b) | 0 | 67 | (9b) liquid | 5.9 | 18.05 | −22.27 | 15 min |
| EtSCH$_2$CH$_2$OCH$_2$CH$_2$OH (8c) | 28 | 83 | (9c) liquid | 5.7 | 18.16 | −22.68 | 15 min |
| t-BuSCH$_2$CH$_2$OCH$_2$CH$_2$OH (8d) | 11 | 70 | (9d) liquid | 5.5 | 17.94 | −26.21 | 15 min |
| i-AmSCH$_2$CH$_2$OCH$_2$CH$_2$OH (8e) | 0 | 75 | (9e) liquid | 5.0 | 18.09 | −23.03 | 15 min |
| Et—SCH$_2$CH$_2$OCH$_2$CH$_2$OCH$_2$CH$_2$OH (8f) | 23 | 81 | (9f) liquid | 5.2 | 18.07 | −23.48 | 15 min |
| t-BuSCH$_2$CH$_2$OCH$_2$CH$_2$OCH$_2$CH$_2$OH (8g) | 9 | 68 | (9g) liquid | 4.2 | 18.28 | −26.20 | 15 min |
| i-AmSCH$_2$CH$_2$OCH$_2$CH$_2$OCH$_2$CH$_2$OH (8h) | 0 | 66 | (9h) liquid | 4.0 | 18.13 | −23.22 | 15 min |
| H$_3$COCH$_2$CH$_2$SCH$_2$CH$_2$OH (8i) | 0 | 62 | (9i) liquid | 6.0 | 18.50 | −21.49 | 15 min |

TABLE 3-continued

| | Borane Adducts of Borate Esters of Hydroxydialkylsulfides | | | | | | |
|---|---|---|---|---|---|---|---|
| | | | | borane addition compounds of borate esters | | | |
| | exchange,[a] % | | | $[BH_3]$[b] | $^{11}B$ NMR,[c] δ | | HB of |
| sulfur substituted borate ester | BMS | $BH_3$.THF | state | M | borate | adduct | 1-octene[d] |

[a]BMS or $BH_3$.THF and borate ester mixed at 3:1 molar ratio.
[b]Estimated by hydrolysis in water: glycerol: THF 1:1:1 and measuring hydrogen evolved.
[c]Neat.

The invention claimed is:

1. A novel borane adduct of hydroxydialkylsulfide borate esters represented by the formula

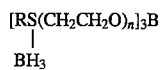

wherein R is straight or branched chain alkyl or alkoxy having from 2 to 5 carbon atoms and n is 1 to 3 inclusive.

2. A compound of claim 1, tris[2-(tert-butylthio)ethyl] borate borane adduct.

3. A compound of claim 1, tris[2-(isoamylthio)ethyl] borate borane adduct.

4. A compound of claim 1, tris[2-[2-(ethylthio) ethoxy] ethyl]borate borane adduct.

5. A compound of claim 1, tris[2-[2-(tert-butylthio) ethoxy]ethyl]borate borane adduct.

6. A compound of claim 1, tris[2-[2-(isoamylthio) ethoxy] ethyl]borate borane adduct.

7. A compound of claim 1, tris[2-[2-[2-(ethylthio)ethoxy] ethoxy]ethyl]borate borane adduct.

8. A compound of claim 1, tris[2-[2-[2-(tert-butylthio)ethoxy]ethoxy]ethyl]borate borane adduct.

9. A compound of claim 1, tris[2-[2-[2-(isoamylthio) ethoxy]ethoxy]ethyl]borate borane adduct.

10. A compound of claim 1, tris[2-(2-methoxyethylthio) ethyl]borate borane adduct.

* * * * *